(12) United States Patent
Alupei et al.

(10) Patent No.: US 7,858,748 B2
(45) Date of Patent: Dec. 28, 2010

(54) METHOD FOR PURIFYING MARINE COLLAGEN AND THE PROCESSING THEREOF INTO POROUS SPONGES

(75) Inventors: Corneliu Iulian Alupei, Neuwied (DE); Peter Ruth, Melsbach (DE); Christian Rohrer, Linz (AT); Wolfgang Schatton, Frankfurt (DE)

(73) Assignee: Lohmann & Rauscher GmbH & Co. KG, Neuwied (DE)

( * ) Notice: Subject to any disclaimer, the term of this patent is extended or adjusted under 35 U.S.C. 154(b) by 0 days.

(21) Appl. No.: 12/652,767

(22) Filed: Jan. 6, 2010

(65) Prior Publication Data

US 2010/0105881 A1    Apr. 29, 2010

Related U.S. Application Data

(62) Division of application No. 11/817,044, filed as application No. PCT/EP2006/001313 on Feb. 14, 2006, now Pat. No. 7,687,604.

(30) Foreign Application Priority Data

Feb. 24, 2005  (DE)  .................. 10 2005 008 416

(51) Int. Cl.
*A61K 38/17* (2006.01)
*C09H 1/00* (2006.01)
(52) U.S. Cl. ..................................... 530/356
(58) Field of Classification Search ........................ None
See application file for complete search history.

(56) References Cited

U.S. PATENT DOCUMENTS 6,660,280 B1    12/2003    Allard et al.
2003/0032601 A1    2/2003    Kreuter et al.

FOREIGN PATENT DOCUMENTS

WO    01/64046 A2    9/2001

OTHER PUBLICATIONS

Dieter Swatschek et al., "Marine sponge collagen: isolation, characterization and effects on the skin parameters surface-pH, moisture and sebum", European Journal of Pharmaceutics and Biopharmaceutics, vol. 53, No. 1, pp. 107-113, (2002).

Dieter Swatschek et al., "Microparticles derived from marine sponge collagen (SCMPs): preparation, characterization and suitability for dermal delivery of all-trans retinol", European Journal of Pharmaceutics and Biopharmaceutics, vol. 54, No. 2, pp. 125-133, (2002).

International Search Report and opinion, dated Aug. 8, 2007 concerning counterpart International Application No. PCT/EP2006/001313.

*Primary Examiner*—Suzanne M. Noakes
(74) *Attorney, Agent, or Firm*—Panitch Schwarze Belisario & Nadel LLP

(57) ABSTRACT

Methods are provided for purifying marine collagen and for processing the collagen into porous sponges. Products produced with these methods and the use of the products are also provided.

9 Claims, No Drawings

METHOD FOR PURIFYING MARINE COLLAGEN AND THE PROCESSING THEREOF INTO POROUS SPONGES

CROSS-REFERENCE TO RELATED APPLICATIONS

This application is a Divisional Application of U.S. application Ser. No. 11/817,044 which is a Section 371 of International Application No. PCT/EP2006/001313, filed Feb. 14, 2006, which was published in the German language on Aug. 31, 2006, under International Publication No. WO 2006/089660 A2, and the disclosures of which are incorporated herein by reference.

BACKGROUND OF THE INVENTION

The present invention relates to a method for purifying marine collagen, especially for enhancing the smell and appearance of marine collagen.

The invention further relates to a method for the production of porous sponges of marine collagen which are suitable in particular for medical purposes.

Collagen is a biodegradable as well as biocompatible protein which is used as a starting material for manifold applications in the food industry, in the pharmaceutical and cosmetic industries as well as in medicine.

"Marine collagen" is understood to mean collagen isolated from marine organisms, that is, organisms living in the sea, especially from members of the Porifera strain, preferably from *Chondrosia reniformis*.

A large number of collagen products are known and being utilized in medicine. Such products include, for example, sponges, fibers or membranes.

The vast majority of these products is manufactured from collagen which is produced from the connective tissue, the skin, the bones, or the tendons of mammals, for example from cattle, horses or pigs. The essential disadvantages of these products are to be seen in the facts that:

in most cases, a young animal has to be used as the source for the collagen in order to obtain a sufficient yield of collagen;

the collagen obtained is in most cases soluble both in acid media as well as in basic media, which necessitates an additional crosslinking reaction (physically, by heat treatment, or chemically, by using bifunctional substances) in order to enhance the mechanical properties of the collagen and its stability in liquid media;

there is a risk of contamination with bovine spongiform encephalopathy (BSE).

As an alternative to producing collagen from mammals, International patent application publication WO 01/64046 describes a method for isolating collagen from marine sponges of the genus *Chondrosia reniformis* (Porifera, Demospongiae).

In this method, fresh sponge starting material is imbibed in alcohol and then washed with water, and an extracting agent is added thereto, preferably at a pH of 7-12. The resultant collagen extract is processed by increasing the pH of the suspension to a value of 8-11, stirring, centrifuging, subsequently lowering the pH value of the supernatant, as well as centrifuging and isolating the precipitate.

The sponge collagen obtainable by this method does, however, have disadvantages consisting essentially in that:

the collagen solution has a dirty appearance;

the collagen is microbiologically impure; and products from this sponge collagen have an unpleasant smell.

BRIEF SUMMARY OF THE INVENTION

The task underlying the present invention thus was to eliminate the above-mentioned disadvantages of marine collagen and to provide collagen from marine organisms, which is also suitable for the manufacture of products for medicinal purposes.

This task is solved by a method wherein a collagen precipitate is purified by using chemical treatment steps, thereby enhancing the smell and appearance thereof. The purified collagen can subsequently be processed into porous sponges by lyophilization.

According to the present invention, the method for purifying marine collagen encompasses treating a collagen precipitate, as obtainable, for example, according to the method described in WO 01/64046, with hydrogen peroxide in aqueous solutions at different pH values.

To this end, the moisture of the collagen precipitate should initially be adjusted to a content of 70 to 95% by weight, preferably to a content of 80 to 90% by weight. This can be accomplished by wringing the collagen precipitate under pressure or by centrifugation, in order to reduce the moisture content of the collagen precipitate to the desired content, if necessary.

The collagen precipitate is then suspended in an aqueous $H_2O_2$ solution containing 0.1 to 1% (v/v), preferably 0.5% (v/v), of $H_2O_2$. Then the pH of the collagen suspension is adjusted to a value of from 11 to 13. This causes the collagen to dissolve.

Following incubation of the collagen with $H_2O_2$ under alkaline conditions, the collagen solution is filtered to remove insoluble components. Thereafter, the collagen is precipitated from the solution by adding a suitable water-miscible organic solvent to the solution.

The collagen precipitate is filtered off, and its moisture content is readjusted to 70-95% by weight, preferably 80 to 90% by weight. Then, the collagen is again dissolved in an aqueous $H_2O_2$ solution, which has a content of $H_2O_2$ of 0.1 to 1% (v/v), preferably of 0.5% (v/v), and the pH of this collagen solution is adjusted to a value of from 5 to 7, so that the collagen may then be used for the production of sponges, membranes or fibers for medical purposes.

Adjustment of the pH to a value of from 11 to 13 is preferably accomplished with NaOH, but it may also be accomplished with other alkali hydroxides or alkaline earth hydroxides, such as KOH, $Ca(OH)_2$ or $Mg(OH)_2$.

As water-miscible organic solvents, ethanol and isopropanol are preferred. Precipitation is preferably performed at a ratio of water to ethanol which is between 1:2 and 1:3.

Neutralization of the collagen solution to a pH of 5 to 7 may be accomplished by reducing the pH value by adding organic acids, e.g., formic acid, acetic acid, citric acid, ascorbic acid, propionic acid, lactic acid, or inorganic acids, such as hydrochloric acid, phosphoric acid or sulfuric acid. Preferably, the pH value is adjusted by addition of 5 N hydrochloric acid.

The advantages of the method according to the invention are:

a high yield in protein extraction;

a sterile collagen which is free of bacteria;

a BSE-free collagen since Porifera have no neural structures;

a collagen with a pleasing appearance which does not look dirty;

a collagen without unpleasant smell;

a collagen which is insoluble in acid media and which does not necessitate an additional crosslinking reaction in order to improve its mechanical properties and stability in liquids; and a collagen which can be used for the production of dressings for wound healing or as a support in tissue regeneration.

On account of its advantages, the collagen purified by using the method according to the present invention is particularly suitable for the manufacture of products for medical purposes.

Therefore, the collagen purified using the method according to the present invention, as well as the use thereof for the manufacture of porous sponges, fiber material or membranes, are also subject matters of the present invention.

The present invention thus also relates to methods for the production of porous sponges from the purified marine collagen.

Porous collagen sponges may be produced by a method wherein a solution obtained according to the method of the present invention is deep-frozen and freeze-dried after the collagen solution has either been foamed up by vigorous shaking/stirring or after the air contained in the collagen solution has been removed in vacuo, in order to produce sponges with smaller pores. The collagen solution preferably contains collagen at a concentration of 0.5 to 5% by weight.

By using appropriate molds, in which the collagen solution or the collagen foam is frozen, it is possible to produce porous collagen foams of any shape.

Collagen sponges with further enhanced properties, especially with a view to their medical application, can be obtained by acid treatment of the collagen sponges after these have been freeze-dried. Acid treatment is performed with inorganic acids, preferably by immersing the sponge in an 0.1 NHCl solution. Thereafter, the acid-treated sponge can be dehydrated by deep-freezing and freeze-drying, or by immersing in ethanol and air-drying.

Employing the method according to the present invention for producing collagen sponges, it is possible also to produce porous collagen sponges with antimicrobial properties. To this end, an antimicrobially active substance can be added to the collagen suspension prior to deep-freezing. A preferred antimicrobially active substance is silver sulfadiazine, which is added in an amount of 1% by weight, relative to the amount of collagen in the suspension.

As an alternative to the afore-described approach, the porous collagen foams can be immersed, after the acid treatment, in a solution containing an antimicrobially active substance. Subsequently, the collagen sponge can be dehydrated by freeze-drying or, if the antimicrobially active substance is insoluble in ethanol, by immersing in ethanol and subsequent air-drying.

Additional subject matters of the present invention are therefore the porous collagen sponges produced by the aforementioned method and the use of the sponges for the manufacture of products for medicinal purposes, such as wound dressings.

DETAILED DESCRIPTION OF THE INVENTION

The invention will now be described in greater detail with reference to the following specific, non-limiting examples.

Example 1

Method for Purifying Sponge Collagen

A collagen precipitate precipitated in an acid medium (pH 3), which had been obtained in accordance with the method described in WO 01/64046, was separated from the medium by filtration and wrung out under pressure until a residual moisture content of approximately 84% by weight was obtained. The collagen fibers obtained in this manner were freeze-dried for storage at a temperature of approx. −20° C.

121 g of the frozen collagen fibers were suspended in 1300 ml of aqueous 0.5% (v/v) $H_2O_2$ solution while stirring for 2 hours. Then, the pH of the solution was adjusted to a value of 12.4 with a 5N solution of NaOH, in order to dissolve the collagen fibers. The resulting collagen solution was filtered to remove insoluble components and then poured into 2600 ml ethanol (conc. 98%), while stirring vigorously. The collagen thereby precipitated was of a white or slightly yellowish color and had a fibrous appearance.

The collagen fibers were freed from the medium by filtration, wrung out under pressure or by centrifugation and subsequently homogenously suspended in 300 ml of an aqueous 0.5% (v/v) $H_2O_2$ solution, while stirring. The pH of the solution was adjusted to a value of 6.5 with a 5 N HCL solution. Adjustment of the pH was performed while stirring vigorously, in order to avoid formation of fiber precipitates. In this manner, a sterile collagen solution with a collagen concentration of 2.8% by weight was obtained.

All method steps were performed at room temperature, and all objects coming into contact with the collagen were rinsed with an 0.5% by weight $H_2O_2$ solution before being used.

Example 2

Production of Porous Sponges Using Purified Sponge Collagen

A solution of sponge collagen with a collagen concentration of 2% by weight and a pH value of 6.5, which had been obtained using a method according to Example 1, was foamed by vigorous stirring with the aid of an Ultra Turrax. The collagen foam was cast into a rectangular mold made of polypropylene or polystyrene. The heights of the foam layers varied between 2 and 8 mm. The collagen foam was frozen in the mold at −40° C. and then lyophilized.

Example 3

Production of Sponges on the Basis of Precipitated Sponge Collagen

Porous sponges of sponge collagen were produced as described in Example 2. Subsequently, the freeze-dried sponges were subjected to a 30 minute acid treatment by immersion in an 0.1 N HCl solution. Following this treatment, the sponges were repeatedly washed with distilled water until the last residues of acid were removed.

These sponges were frozen in a still moist state and dried by lyophilization.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A marine collagen purified in accordance with a method comprising the steps:
   adjusting a moisture content of a collagen precipitate, which has been precipitated in an acid medium, to 70 to 95% by weight;
   suspending the precipitated collagen in a first aqueous $H_2O_2$ solution;

solubilizing the suspended collagen by adjusting a pH of the collagen suspension to a value of from 11 to 13;

reprecipitating the suspended collagen with an organic, water-miscible solvent;

filtering off of the reprecipitated collagen;

adjusting a moisture content of the reprecipitated collagen to 70 to 95% by weight;

resuspending the reprecipitated collagen in a second aqueous $H_2O_2$ solution; and adjusting the pH of the resuspended collagen to a value of from 5 to 7.

2. A porous sponge produced from the marine collagen of claim 1, wherein the porous sponge is produced in accordance with a production method comprising the steps:

foaming a solution of the marine collagen or degassing the solution of the marine collagen in vacuo;

optionally placing the solution of the marine collagen in a mold;

deep-freezing the foamed or degassed collagen solution, thereby forming a collagen sponge; and lyophilizing the collagen sponge.

3. The porous sponge according to claim 2, wherein the solution has a collagen content of 0.5 to 5% by weight.

4. The porous sponge according to claim 2, further comprising an antimicrobially active substance in the sponge.

5. The porous sponge according to claim 4, wherein the antimicrobially active substance is present in an amount of about 1% by weight, relative to the collagen content of the sponge.

6. The porous sponge according to claim 4, wherein the antimicrobially active substance comprises silver sulfadiazine.

7. The porous sponge according to claim 2, wherein the production method further comprises treating the collagen sponge, subsequent to the lyophilization thereof, with an inorganic acid, and thereafter washing out the collagen sponge with water until there is no longer any acid detectable.

8. The porous sponge according to claim 7, wherein the inorganic acid is an approximately 0.1 N HCl solution.

9. The porous sponge according to claim 2, having a form of a medical product.

* * * * *